(12) United States Patent
Tomatsu

(10) Patent No.: US 11,070,772 B2
(45) Date of Patent: Jul. 20, 2021

(54) ENDOSCOPE IMAGE-CAPTURING DEVICE AND ENDOSCOPE DEVICE

(71) Applicant: Sony Olympus Medical Solutions Inc., Tokyo (JP)

(72) Inventor: Kei Tomatsu, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 247 days.

(21) Appl. No.: 15/198,351

(22) Filed: Jun. 30, 2016

(65) Prior Publication Data

US 2017/0006264 A1    Jan. 5, 2017

(30) Foreign Application Priority Data

Jul. 2, 2015    (JP) .............................. JP2015-133614

(51) Int. Cl.
*H04N 7/22* (2006.01)
*A61B 1/00* (2006.01)
(Continued)

(52) U.S. Cl.
CPC ............ *H04N 7/22* (2013.01); *A61B 1/00048* (2013.01); *A61B 1/045* (2013.01); *A61B 1/0669* (2013.01);
(Continued)

(58) Field of Classification Search
CPC ..... A61B 1/00096; A61B 1/05; A61B 1/0684; A61B 1/07; A61B 1/018; A61B 1/04; A61B 1/00009; A61B 1/051; A61B 1/00172; A61B 1/00188; A61B 1/0615; A61B 1/0669; A61B 1/0676; A61B 34/30; A61B 34/03; A61B 1/00165; A61B 18/24; A61B 1/012; A61B 5/0059; A61B 1/00016; A61B 5/0071; A61B 5/0084; A61B 1/0002; A61B 5/0075; A61B 18/20; A61B 10/02; A61B 1/0011; A61B 1/015; A61B 1/00181; A61B 1/00105; A61B 1/00124; A61B 1/00091; A61B 1/00048; A61B 1/0008; A61B 1/00112; A61B 1/045; A61B 2505/05;
(Continued)

(56) References Cited

U.S. PATENT DOCUMENTS 5,575,757 A * 11/1996 Kennedy ............ A61B 1/00188
348/65
6,030,339 A     2/2000 Tatsuno et al.
(Continued)

FOREIGN PATENT DOCUMENTS

JP     60-208726 A    10/1985
JP     10-258034 A     9/1998
(Continued)

OTHER PUBLICATIONS

Japanese Office Action dated Mar. 12, 2019 in Japanese Patent Application No. 2015-133614, 4 pages.

*Primary Examiner* — Tat C Chio
(74) *Attorney, Agent, or Firm* — Xsensus, LLP

(57) ABSTRACT

An endoscope image-capturing device includes: a first case inside of which is sealed; an image sensor arranged inside the first case; an electro-optic conversion element arranged outside the first case and configured to convert an image signal output from the image sensor into an optical signal; and a sealing member sealing the electro-optic conversion element.

15 Claims, 15 Drawing Sheets

(51) Int. Cl.
*A61B 1/045* (2006.01)
*A61B 1/06* (2006.01)
*H04N 5/225* (2006.01)
*H04N 5/232* (2006.01)
*H04N 7/015* (2006.01)

(52) U.S. Cl.
CPC .......... *H04N 5/2252* (2013.01); *H04N 7/015* (2013.01); *H04N 2005/2255* (2013.01)

(58) Field of Classification Search
CPC ... A61B 2576/02; A61B 5/004; A61B 5/0066; G01M 3/005; G01M 3/38; G06T 15/20; G06T 2210/41; G01B 9/02091; G01B 9/02007; G01B 9/02014; G01B 11/005; G01B 11/2518; G01B 11/2527; G01B 11/2536; G01B 2290/70; C08L 71/02; A61L 24/046; A61L 31/06; A61L 2300/442; A61L 2400/06; A61L 24/001; A61L 24/0005; A61L 31/14; A61L 2300/416; A61L 2300/434; H01S 3/042; H01S 3/063; H01S 3/08095; H01S 3/1643; H01S 3/2333; H01S 3/2383; H01S 5/10; H01S 5/50; H01S 3/0621; H01S 3/094057; H01S 3/0941; H01S 3/1611; H01S 3/1618; H04N 7/22; H04N 5/2252; H04N 7/015; H04N 2005/2255
See application file for complete search history.

(56) References Cited

U.S. PATENT DOCUMENTS

| | | | |
|---|---|---|---|
| 6,458,078 B1 | 10/2002 | Lüdtke et al. | |
| 8,206,407 B2* | 6/2012 | Onuki | A61B 17/0401 606/139 |
| 8,345,092 B2* | 1/2013 | Takasaki | A61B 1/053 257/680 |
| 8,414,474 B2* | 4/2013 | Chen | A61B 1/00177 600/109 |
| 8,810,638 B2* | 8/2014 | Allen | A61B 1/00183 348/65 |
| 9,005,113 B2* | 4/2015 | Scott | A61B 1/00193 600/102 |
| 9,247,867 B2* | 2/2016 | Baum | A61B 1/00013 |
| 2004/0092978 A1* | 5/2004 | Surti | A61B 17/1285 606/157 |
| 2004/0210108 A1* | 10/2004 | Shimizu | A61B 1/00188 600/112 |
| 2006/0259044 A1* | 11/2006 | Onuki | A61B 17/0401 606/139 |
| 2007/0019156 A1* | 1/2007 | Fink | A61B 3/16 351/200 |
| 2007/0286231 A1 | 12/2007 | Kubo et al. | |
| 2008/0080051 A1* | 4/2008 | Yamamoto | A61B 1/05 359/513 |
| 2009/0149715 A1* | 6/2009 | Mao | A61B 5/411 600/202 |
| 2010/0066235 A1* | 3/2010 | Ooyama | H01J 29/86 313/496 |
| 2010/0073470 A1* | 3/2010 | Takasaki | A61B 1/053 348/76 |
| 2010/0245549 A1* | 9/2010 | Allen | A61B 1/00183 348/65 |
| 2010/0261961 A1* | 10/2010 | Scott | A61B 1/00193 600/111 |
| 2011/0263942 A1* | 10/2011 | Chen | G02B 23/2461 600/178 |
| 2011/0285866 A1* | 11/2011 | Bhrugumalla | H04N 5/23235 348/218.1 |
| 2012/0320176 A1* | 12/2012 | Tanaka | A61B 1/00006 348/65 |
| 2013/0012777 A1* | 1/2013 | Baum | A61B 1/00013 600/110 |
| 2014/0018613 A1* | 1/2014 | Scott | A61B 1/00193 600/102 |
| 2014/0142383 A1* | 5/2014 | Blumenzweig | A61B 1/00105 600/110 |
| 2014/0213850 A1* | 7/2014 | Levy | A61B 1/00137 600/156 |
| 2014/0296643 A1* | 10/2014 | Levy | A61B 1/00096 600/160 |
| 2015/0065800 A1 | 3/2015 | Jungbauer et al. | |
| 2015/0085094 A1* | 3/2015 | Fujimori | H01L 25/042 348/65 |
| 2015/0148608 A1* | 5/2015 | Fukushima | A61B 1/00068 600/116 |
| 2015/0190037 A1* | 7/2015 | Scott | A61B 1/00193 348/45 |
| 2015/0245763 A1* | 9/2015 | Kido | A61B 1/0011 600/109 |
| 2015/0313679 A1* | 11/2015 | Fukushima | G05B 15/02 600/102 |
| 2016/0220107 A1* | 8/2016 | Scott | A61B 1/00193 |
| 2017/0049301 A1* | 2/2017 | Hagihara | A61B 1/04 |
| 2017/0172394 A1* | 6/2017 | Scott | A61B 1/00193 |
| 2017/0251990 A1* | 9/2017 | Kheradpir | A61B 6/501 |
| 2018/0084996 A1* | 3/2018 | Su | A61B 3/14 |

FOREIGN PATENT DOCUMENTS

| | | |
|---|---|---|
| JP | 2005-66129 | 3/2005 |
| JP | 2008-11504 A | 1/2008 |
| JP | 2012-245045 | 12/2012 |
| JP | 2014-198144 A | 10/2014 |
| JP | 2015-519937 A | 7/2015 |
| WO | WO 2013/027408 A1 | 2/2013 |

* cited by examiner

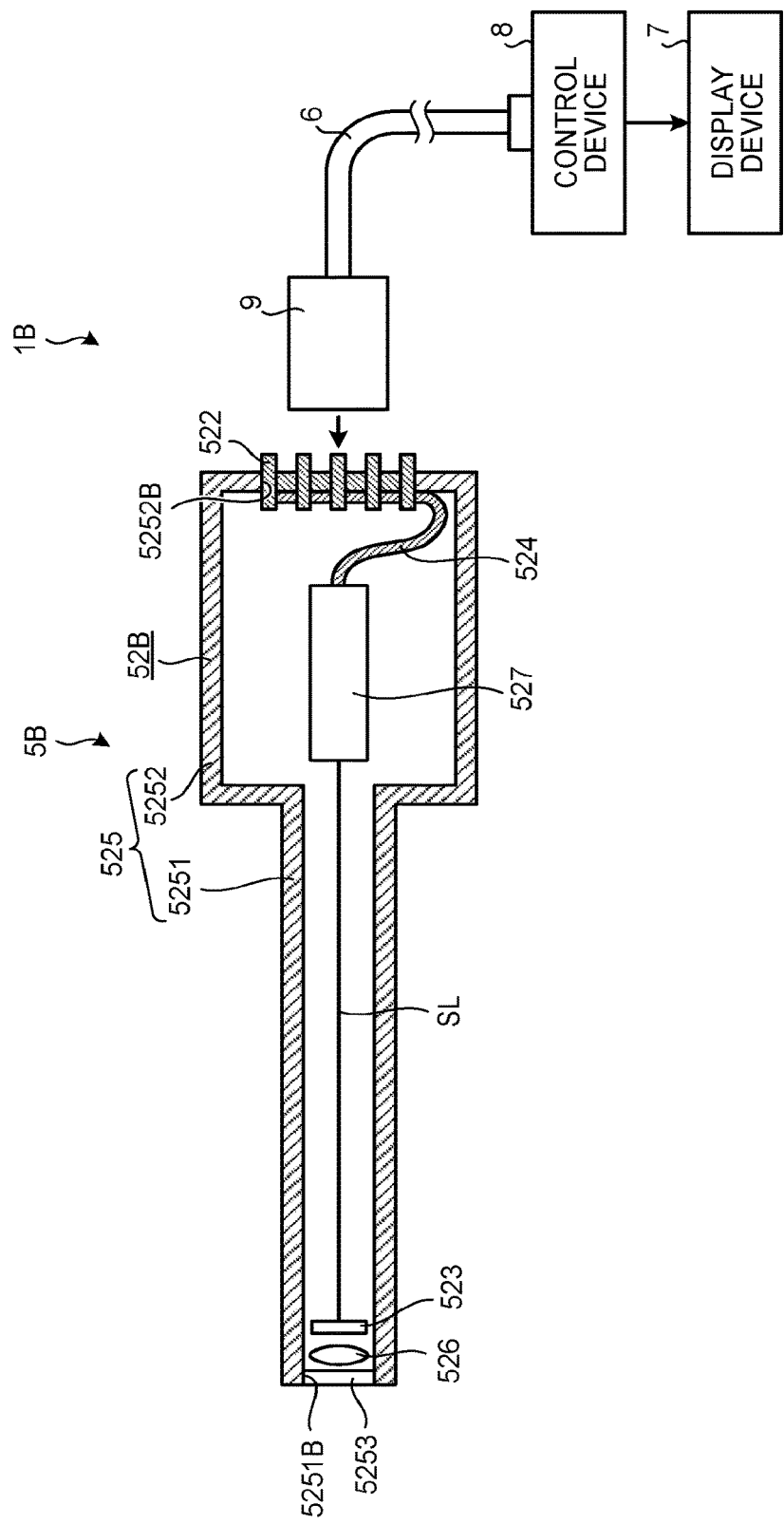

ENDOSCOPE IMAGE-CAPTURING DEVICE AND ENDOSCOPE DEVICE

CROSS-REFERENCE TO RELATED APPLICATION(S)

The present application claims priority to and incorporates by reference the entire contents of Japanese Patent Application No. 2015-133614 filed in Japan on Jul. 2, 2015.

BACKGROUND

The present disclosure relates to an endoscope image-capturing device and an endoscope device.

An endoscope device in the medical field captures an image of the inside of an observation target (living body) such as a human by using an image sensor so as to observe the inside of this living body (refer to Japanese Patent Application Laid-open No. 2012-245045 and Japanese Patent Application Laid-open No. 2005-66129, for example).

The endoscope device (endoscope system) disclosed in Japanese Patent Application Laid-open No. 2012-245045 is a head-separated endoscope device including an insertion unit (endoscope scope) inserted into the living body, an endoscope image-capturing device (camera head) including an image sensor configured to capture an object image condensed by the insertion unit, a control device (image processor) configured to process an image signal output from the image sensor, and a cable electrically coupling between the image sensor and the control device.

In order to protect the image sensor of the endoscope image-capturing device against a medicinal solution used in sterilization involving wiping and liquid immersion and high-temperature and high-pressure vapor in autoclave processing (high-temperature and high-pressure vapor sterilization), this image sensor is arranged in a sealed casing the inside of which is sealed (held watertightly and airtightly). In the endoscope image-capturing device, a sealing connector such as a waterproof connector or a hermetic connector is attached to an opening of the sealed casing to transmit the image signal from the image sensor arranged inside the sealed casing to the outside of the sealed casing while maintaining the sealability (watertightness and airtightness) of the sealed casing. Then, the image signal from the sealing connector is transmitted to a control device such as an image processor through a cable (refer to Japanese Patent Application Laid-open No. 2012-245045).

Similarly to the endoscope device disclosed in Japanese Patent Application Laid-open No. 2012-245045, an endoscope device disclosed in Japanese Patent Application Laid-open No. 2005-66129 is a head-separated endoscope device.

The endoscope image-capturing device (camera head) disclosed in Japanese Patent Application Laid-open No. 2005-66129 is provided, inside this endoscope image-capturing device, with an electro-optic conversion element (E/O converter) configured to convert an image signal (electric signal) from the image sensor into an optical signal. The endoscope image-capturing device is configured to transmit the image signal from the image sensor as the optical signal to the control device through the cable. Transmission of the image signal as an optical signal is advantageous, in particular, for an increase in the data amount of the image signal for high image quality such as what is called 4K and 8K and a speeding up of signal transmission.

SUMMARY

When the endoscope image-capturing device using the sealed casing disclosed in Japanese Patent Application Laid-open No. 2012-245045 employs the optical transmission as disclosed in Japanese Patent Application Laid-open No. 2005-66129, the following problem occurs.

The sealing connector disclosed in Japanese Patent Application Laid-open No. 2012-245045 includes a plurality of conductive pins penetrating between the inside and outside of the sealed casing. These conductive pins electrically couple the image sensor and the cable (control device). In other words, a typical sealing connector transmits an electric signal.

An additional configuration that enables transmission of an optical signal complicates the configuration of the disclosed sealing connector, resulting in an increase in the cost and size of the sealing connector.

The electro-optic conversion element includes a light source configured to emit light such as laser light. This light source is repeatedly turned on and off in optical communication, and thus typically has a lifetime shorter than that of the image sensor. When the image sensor and the electro-optic conversion element are provided in the same sealed casing, a sealed structure (sealed casing) necessary for the image sensor needs to be temporarily unlocked to replace the electro-optic conversion element due to its failure and lifetime, and after the replacement, the sealability needs to be achieved again, which is reflected on the cost of the replacement.

For this reason, the following configuration is preferred to achieve the optical transmission as disclosed in Japanese Patent Application Laid-open No. 2005-66129 with the endoscope image-capturing device disclosed in Japanese Patent Application Laid-open No. 2012-245045.

Specifically, the electro-optic conversion element is provided outside the sealed casing. An image signal from the image sensor is transmitted as an electric signal to the outside of the sealed casing through the sealing connector. Then, this image signal (electric signal) is converted into an optical signal by the electro-optic conversion element arranged outside the sealed casing. Then, this optical signal is transmitted to the control device through the cable.

However, with this configuration as described above, the electro-optic conversion element is provided outside the sealed casing, making it difficult to protect the electro-optic conversion element against a medicinal solution used in sterilization involving wiping and liquid immersion and high-temperature and high-pressure vapor in autoclave processing.

There is a need for an endoscope image-capturing device and an endoscope device that each achieve a small configuration that optically transmits an image signal at low cost, and protect the electro-optic conversion element against a medicinal solution used in sterilization involving wiping and liquid immersion and high-temperature and high-pressure vapor in autoclave processing.

An endoscope image-capturing device according to one aspect of the present disclosure includes: a first case inside of which is sealed; an image sensor arranged inside the first case; an electro-optic conversion element arranged outside the first case and configured to convert an image signal output from the image sensor into an optical signal; and a sealing member sealing the electro-optic conversion element.

BRIEF DESCRIPTION OF THE DRAWINGS

FIG. 15 illustrates modification 2 of the embodiment of the present disclosure.

DETAILED DESCRIPTION

Figure 1:
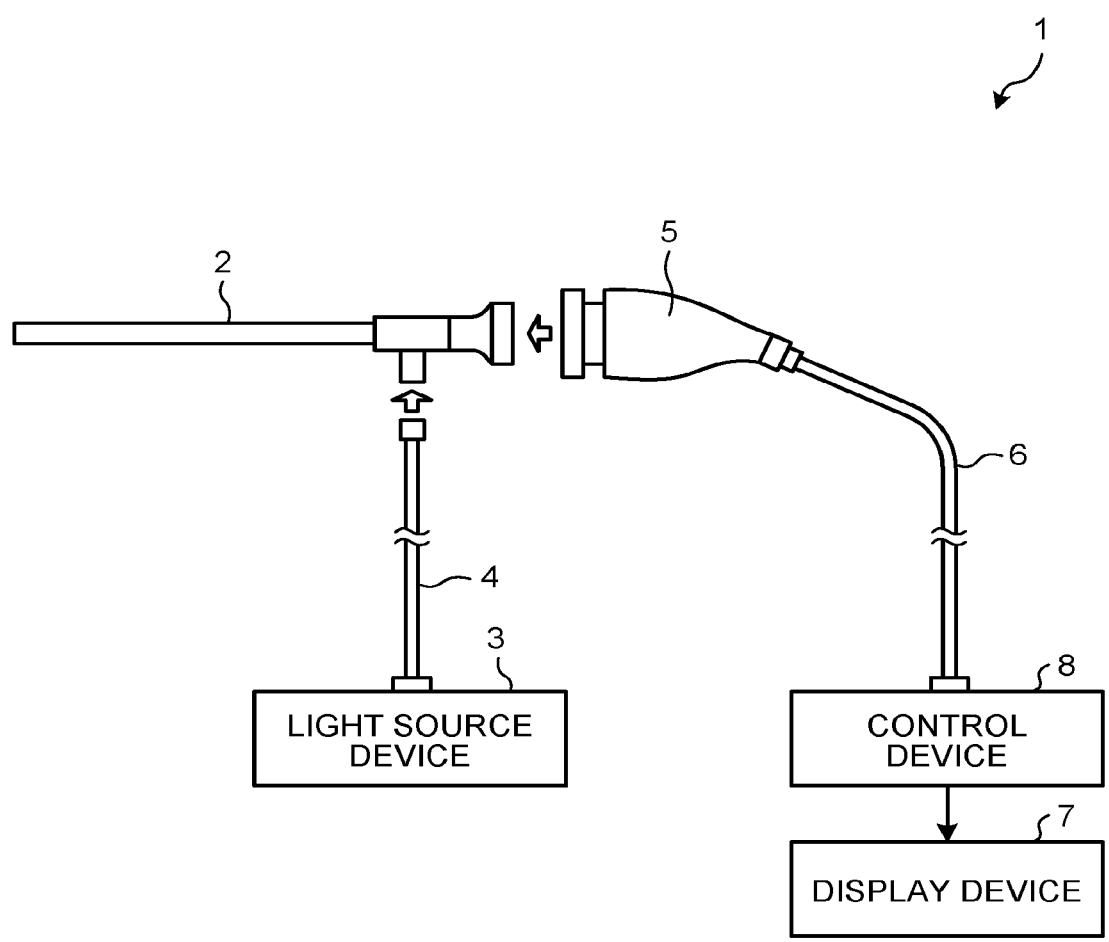
FIG. 1 illustrates a schematic configuration of an endoscope device according to an embodiment of the present disclosure.

Modes (hereinafter referred to as embodiments) for carrying out the present disclosure will be described below with reference to the accompanying drawings. The embodiments described below do not limit the present disclosure. Any identical parts in the drawings are denoted by identical reference numerals.

Schematic Configuration of Endoscope Device

FIG. 1 illustrates a schematic configuration of an endoscope device 1 according to an embodiment of the present disclosure.

The endoscope device 1 is used in the medical field to observe the inside of an observation target (living body) such as a human.

As illustrated in FIG. 1, the endoscope device 1 includes an insertion unit 2, a light source device 3, a light guide 4, a camera head 5, a composite cable 6, a display device 7, and a control device 8.

The insertion unit 2 is hard and elongated, and inserted into the living body. An optical system for condensing an object image is provided in the insertion unit 2.

The light source device 3 is coupled with one end of the light guide 4 to supply, through this one end of the light guide 4, light for illuminating inside the living body.

The light guide 4 has one end detachably coupled with the light source device 3, and the other end detachably coupled with the insertion unit 2. The light guide 4 transfers the light supplied from the light source device 3 from the one end to the other end so as to supply the light to the insertion unit 2. The light supplied to the insertion unit 2 is emitted through a head of this insertion unit 2 to irradiate inside the living body. Then, the light (object image) emitted to the inside of the living body is condensed through the optical system in the insertion unit 2.

The camera head 5 has the functionality of an endoscope image-capturing device according to the present disclosure. The camera head 5 is detachably coupled with a base end of the insertion unit 2. Under control of the control device 8, the camera head 5 captures the object image condensed through the insertion unit 2 and performs an electro-optic conversion on an image signal (electric signal) through this image capturing to obtain and output an optical signal.

The configuration of the camera head 5 is described later in detail.

The composite cable 6 includes a plurality of optical fibers 61 (refer to FIG. 6) and a plurality of electric signal cables 62 (refer to FIG. 6) under an outer cover 60 (refer to FIG. 6) as an outermost layer. The composite cable 6 has one end detachably coupled with the control device 8 and the other end coupled with the camera head 5.

The optical fibers 61 are arranged at a central position when viewed in a cross-section of the composite cable 6, and communicate an optical signal between the camera head 5 and the control device 8.

The electric signal cables 62 are arranged at a peripheral part of the optical fibers 61 when viewed in the cross-section of the composite cable 6, and communicate an electric signal between the camera head 5 and the control device 8.

The display device 7 displays an image under control of the control device 8. In the present embodiment, the display device 7 has a monitor size of 55 inches or larger, but the present disclosure is not limited thereto. The display device 7 may have other monitor sizes.

The control device 8 acquires the optical signal (image signal) output from the camera head 5 through each optical fiber 61, and performs an electro-optic conversion on this optical signal into an electric signal. Then, the control device 8 performs predetermined processing on the electric signal provided with the electro-optic conversion and displays the image captured by the camera head 5 on the display device 7. The control device 8 also outputs a control signal or other signals (electric signals) to the camera head 5 through the electric signal cables 62.

Configuration of Camera Head

Figure 2:
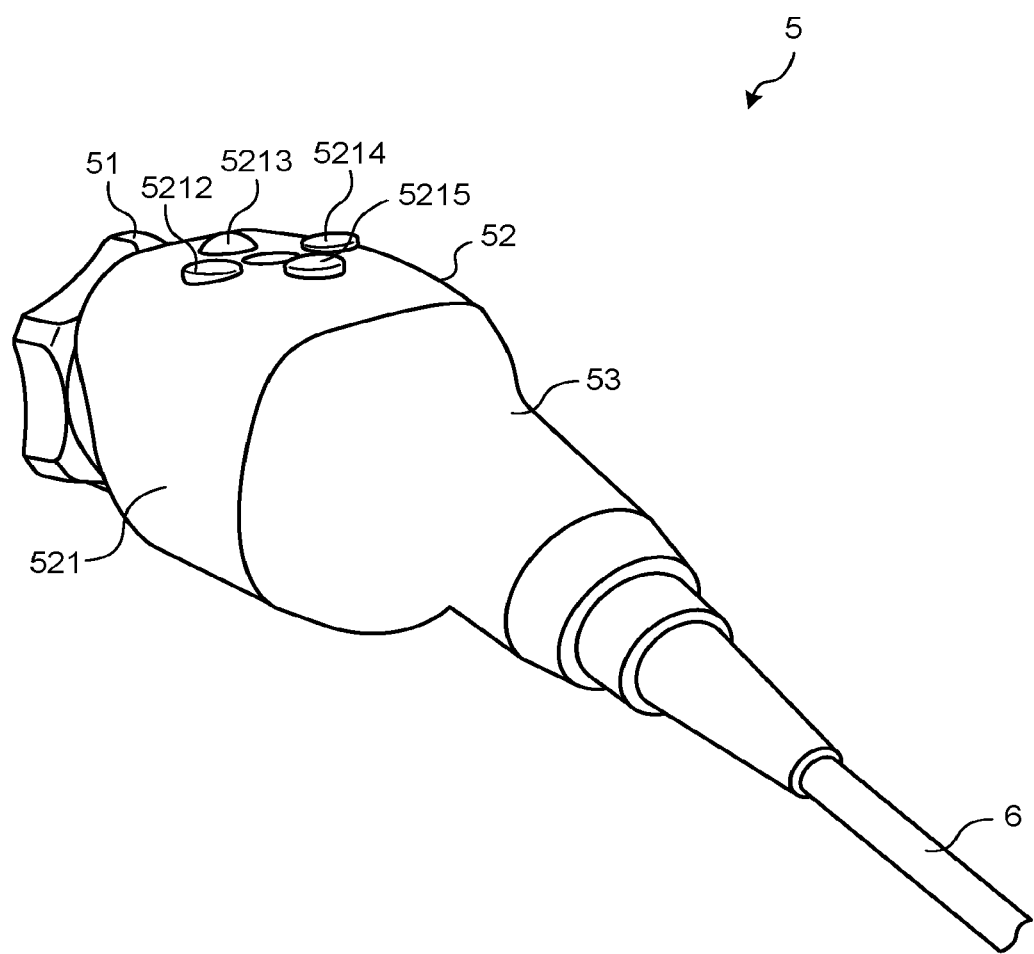
FIG. 2 is a perspective diagram of a camera head illustrated in FIG. 1 when viewed from a base end side (side with which a composite cable is coupled)

FIG. 2 is a perspective diagram of the camera head 5 when viewed from a base end side (side with which the composite cable 6 is coupled).

Figure 6:
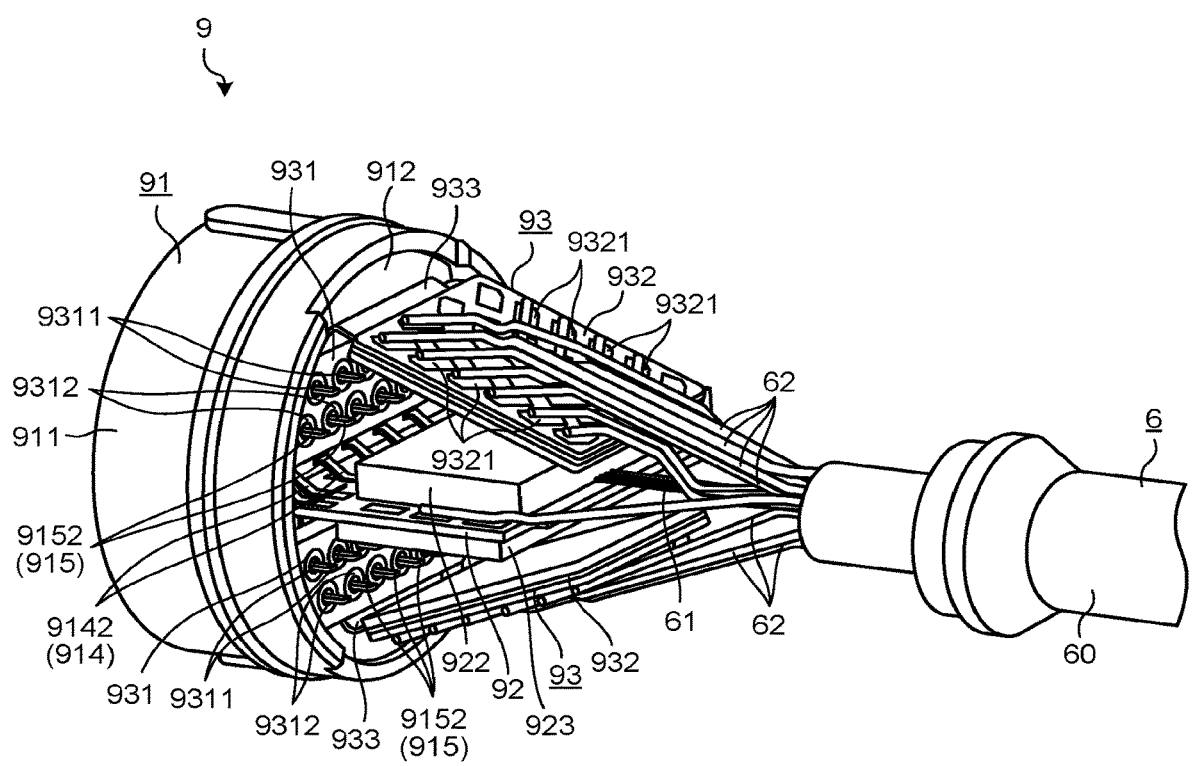
FIG. 6 is a perspective diagram of the internal structure of the electro-optic combined module illustrated in FIG. 5 when viewed from a base end side (side with which the composite cable coupled)

As illustrated in FIG. 2, the camera head 5 includes a coupler 51, a sealed unit 52, and an electro-optic combined module 9 (refer to FIG. 6).

In FIG. 2, a tubular cover 53 covering a base end side of the sealed unit 52 and the electro-optic combined module 9 is attached, and thus the electro-optic combined module 9 is not illustrated.

The coupler 51 is used to detachably couple the camera head 5 with the base end of the insertion unit 2, and is provided to the head of the camera head 5.

Figure 3:
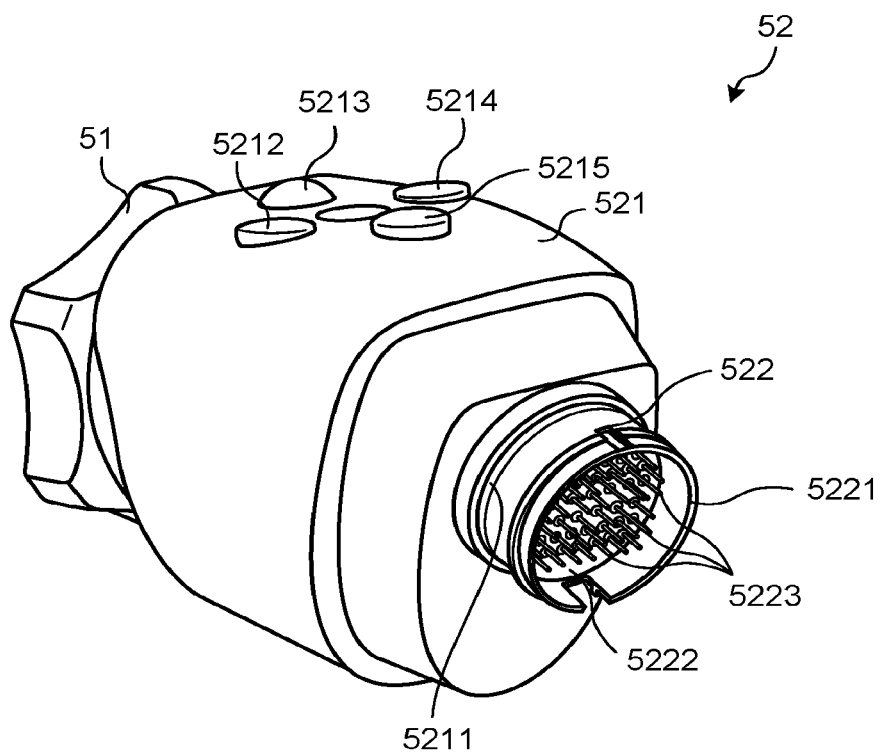
FIG. 3 is a perspective diagram of a sealed unit illustrated in FIG. 2 when viewed from a base end side (side with which an electro-optic combined module is coupled)

FIG. 3 is a perspective diagram of the sealed unit 52 when viewed from a base end side (side with which the electro-optic combined module 9 is coupled).

Figure 4:
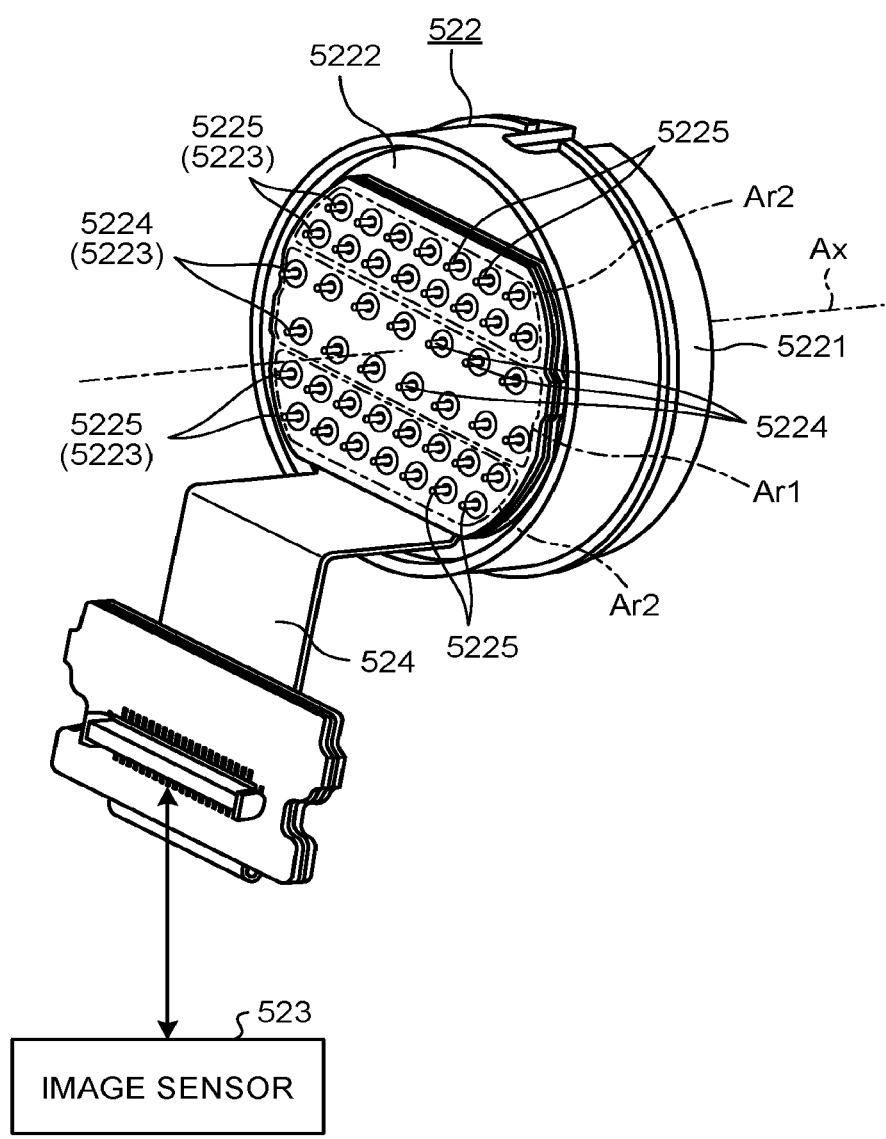
FIG. 4 is a perspective diagram of a sealing connector illustrated in FIG. 3 when viewed from the inside of the sealed unit.

As illustrated in FIG. 2 or 3, the sealed unit 52 includes a sealed-unit side case 521, a sealing connector 522 (FIG. 3), and an image sensor 523 (refer to FIG. 4).

The sealed-unit side case 521 has the functionality of a first case according to the present disclosure. The sealed-unit side case 521 is made of, for example, titanium, titanium alloy, or stainless steel alloy. As illustrated in FIG. 3, the sealed-unit side case 521 is a rectangular housing having openings 5211 (FIG. 3 illustrates the opening 5211 on a base end side only) on its head side (side with which the base end of the insertion unit 2 is coupled) and its base end side (side with which the electro-optic combined module 9 is coupled).

The opening (not illustrated) on the head side is sealed with a translucent member (not illustrated) such as glass that transmits the object image condensed through the insertion unit 2. As illustrated in FIG. 3, the opening 5211 on the base end side is engaged and sealed with the sealing connector 522. Accordingly, the inside of the sealed-unit side case 521 is sealed with the translucent member and the sealing connector 522 described above.

The sealed-unit side case 521 houses a lens unit (not illustrated), a driving motor (not illustrated), and the image sensor 523.

The lens unit images the object image condensed through the insertion unit 2 on an imaging plane of the image sensor 523. The lens unit is movable in the direction of an optical axis.

In response to a press on each of switches 5212 to 5215 (FIG. 2, FIG. 3) exposed on the outer surface of the sealed-unit side case 521, the driving motor moves the lens unit in the optical axis to perform adjustment of the focal length and focus of the lens unit.

The image sensor 523 includes a charge coupled device (CCD) or a complementary metal oxide semiconductor (CMOS) that receives light condensed through the lens unit and converts the light into an electric signal.

In the present embodiment, only one image sensor 523 is provided, but the present disclosure is not limited thereto, and a plurality of image sensors 523 may be provided. In the present embodiment, the total number of effective pixels as the sum of the numbers of effective pixels of one or a plurality of image sensors 523 is eight megapixels (for example, what is called 4K resolution of 3840×2160 pixels) or larger, but the present disclosure is not limited thereto, and the total numbers of effective pixels may be other numbers.

The sealed structure of the sealed unit 52 including the sealed-unit side case 521 and the sealing connector 522 may be a watertight structure, but includes the image sensor 523, which is expensive and provided with fine adjustment of the optical axis for image capturing with an external and/or internal optical system. In order to reduce any failure due to intrusion of a medicinal solution and vapor into the inside as much as possible, the sealed unit 52 preferably has an airtight structure having a sealing level higher than that of the watertight structure. In this case, the sealing connector 522 is preferably a hermetic connector.

FIG. 4 is a perspective diagram of the sealing connector 522 when viewed from the inside of the sealed unit 52.

The sealing connector 522 has the functionality of a blocking part according to the present disclosure, and as illustrated in FIG. 3, is fixed to the opening 5211 of the sealed-unit side case 521 by welding, for example.

The sealing connector 522 is a circular connector and includes a first outer frame 5221, a plate 5222, and a plurality of conductive pins 5223 as illustrated in FIG. 3 or 4.

The first outer frame 5221 is made of a metal material and has a cylinder shape.

The plate 5222 is made of a metal material and is a circular plate. The plate 5222 blocks the first outer frame 5221.

The conductive pins 5223 each have the functionality of a terminal according to the present disclosure and have a cylindrical shape. The conductive pins 5223 are inserted into a plurality of openings (not illustrated) penetrating between the front and back surfaces of the plate 5222, respectively. These openings, in which the conductive pins 5223 are inserted, are sealed by a plurality of insulating members made of an insulating material such as glass. In other words, the conductive pins 5223 are attached to the plate 5222 while being insulated from each other without conducting with the plate 5222 by the insulating members described above.

In the following, first conductive pins 5224 refer to the conductive pins 5223 provided in a first region Ar1 illustrated by the dashed and single-dotted line in FIG. 4 among the conductive pins 5223. Second conductive pins 5225 refer to the conductive pins 5223 provided in two second regions Ar1 illustrated with the dashed and double-dotted line in FIG. 4 among the conductive pins 5223.

The first region Ar1 includes a central axis Ax in the first outer frame 5221 when viewed in the direction of the central axis Ax (FIG. 4) of the first outer frame 5221, and is a strip-shaped region extending in the horizontal direction in FIG. 4. The two second regions Ar2 are regions other than the first region Ar1 in the first outer frame 5221, and are strip-shaped regions parallel to the first region Ar1 and extending in the horizontal direction in FIG. 4.

The first conductive pins 5224 are arranged side by side in two lines extending in the vertical direction of FIG. 4 in the first region Ar1.

Similarly to the first conductive pins 5224, the second conductive pins 5225 are arranged side by side in two lines extending in the vertical direction of FIG. 4 in each second region Ar2.

As illustrated in FIG. 4, a sealed-unit side printed-circuit board 524 that relays (electrically couples) the conductive pins 5223 and the image sensor 523 is attached to the sealing connector 522 toward the inside of the sealed unit 52.

The sealed-unit side printed-circuit board 524 relays an image signal (electric signal) output from the image sensor 523 to the first conductive pins 5224. The sealed-unit side printed-circuit board 524 also relays, to the image sensor 523, a control signal or other signals (electric signals) output from the control device 8 through the composite cable 6, the electro-optic combined module 9, and the second conductive pins 5225.

Configuration of Electro-Optic Combined Module

Figure 5:
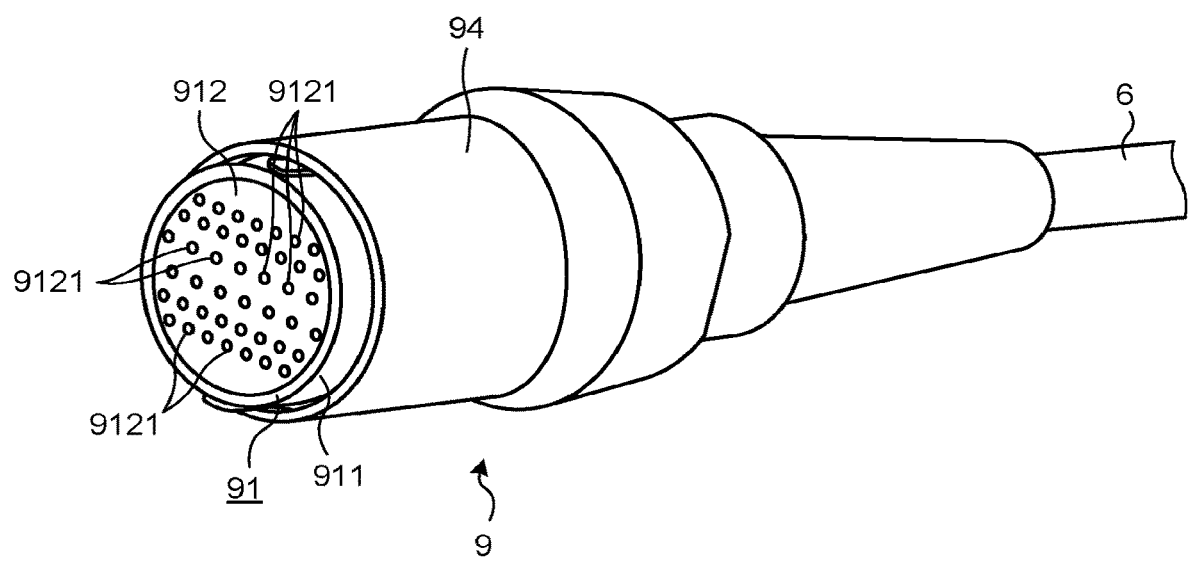
FIG. 5 is a perspective diagram of the electro-optic combined module according to the embodiment of the present disclosure when viewed from a head side (side with which the sealed unit coupled)
Figure 7:
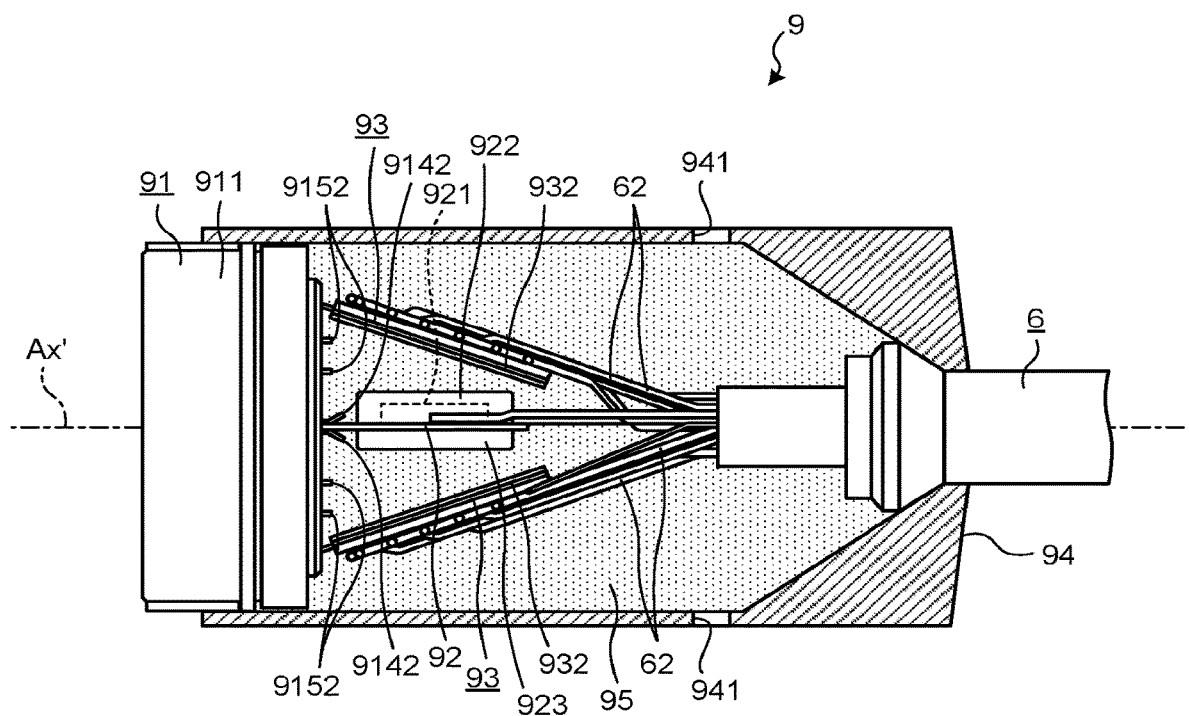
FIG. 7 illustrates the internal structure of the electro-optic combined module illustrated in FIG. 5 when viewed from a side.

FIG. 5 is a perspective diagram of the electro-optic combined module 9 when viewed from a head side (side with which the sealed unit 52 is coupled). FIG. 6 is a perspective diagram of the internal structure of the electro-optic combined module 9 when viewed from a base end side (side with which the composite cable 6 is coupled). FIG. 7 illustrates the internal structure of the electro-optic combined module 9 when viewed from a side.

The electro-optic combined module 9 is mechanically and electrically coupled with the sealing connector 522. The electro-optic combined module 9 converts an image signal (electric signal) output from the image sensor 523 into an optical signal and outputs the optical signal through the composite cable 6 (the optical fibers 61). The electro-optic combined module 9 relays a control signal or other signals (electric signals) output from the control device 8 through the electric signal cables 62, to the sealing connector 522 (the image sensor 523).

As illustrated in FIGS. 5 and 7, the electro-optic combined module 9 includes a receptacle 91, a first printed-circuit board 92 (FIGS. 6 and 7), two second printed-circuit boards 93 (FIGS. 6 and 7), a module-side case 94 (FIGS. 5 and 7), and a filling member 95 (FIG. 7).

For the purpose of illustration, FIG. 6 does not illustrate the module-side case 94, the filling member 95, and a protection member 611 (refer to FIG. 10) to be described later.

Configuration of Receptacle

Figure 8:
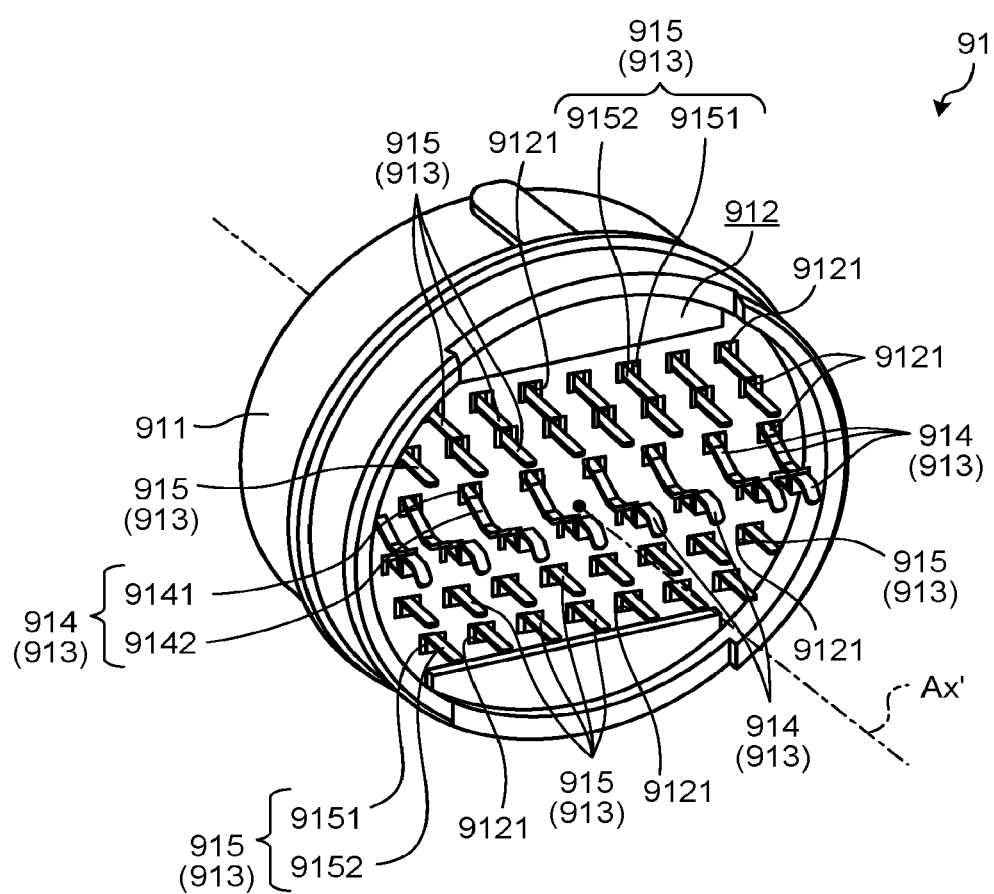
FIG. 8 is a perspective diagram of a receptacle illustrated in FIGS. 5 to 7 when viewed from a base end side (side with which first and second printed-circuit boards are coupled)

FIG. 8 is a perspective diagram of the receptacle 91 when viewed from a base end side (side opposite to a side with which the sealing connector 522 coupled (side with which the first and the second printed-circuit boards 92 and 93 are coupled)).

The receptacle 91 includes a circular connector mechanically and electrically coupled with the sealing connector 522, and is provided to the head of the electro-optic combined module 9.

As illustrated in FIG. 8, the receptacle 91 includes a second outer frame 911, an insulator 912, and a plurality of contacts 913.

The second outer frame 911 is made of a metal material and has a cylindrical shape.

The insulator 912 is made of an insulating material and blocks the second outer frame 911. The insulating material of the insulator 912 is preferably a material that is advantageous in terms of resistance against high temperature, vapor, and sterilization. Examples of such a material include resin such as polypropylene (PP), polyvinylidene chloride (PVDC), polyether ether ketone (PEEK), polyaceta (POM), polyamide (PA) such as nylon, polycarbonate (PC), polytetrafluoroethylene (PTFE), polyimide (PI), polyamide-imide (PAI), polybutylene terephthalate (PBT), and engineering plastic known as PEKEKK (polyether ketone ether ketone ketone), as well as glass and ceramics.

As illustrated in FIG. 5 or 8, the insulator 912 has insertion holes 9121 into which the conductive pins 5223 of the sealing connector 522 may be inserted when the sealing connector 522 and the receptacle 91 are coupled.

The insertion holes 9121 are each formed in such a staged shape that its part on a head side (side with which the sealing connector 522 is coupled) of the receptacle 91 has a circular shape along the shape (cylindrical shape) of the conductive pins 5223 and its part on the base end side of the receptacle 91 has a rectangle shape surrounding this head side in a sectional view when viewed in the direction of a central axis Ax' (FIG. 8) of the second outer frame 911.

As illustrated in FIG. 8, the contacts 913 are provided on a base end side in the insertion holes 9121. The contacts 913 are electrically coupled with the conductive pins 5223 when the conductive pins 5223 of the sealing connector 522 are inserted into the insertion holes 9121.

Figure 9:
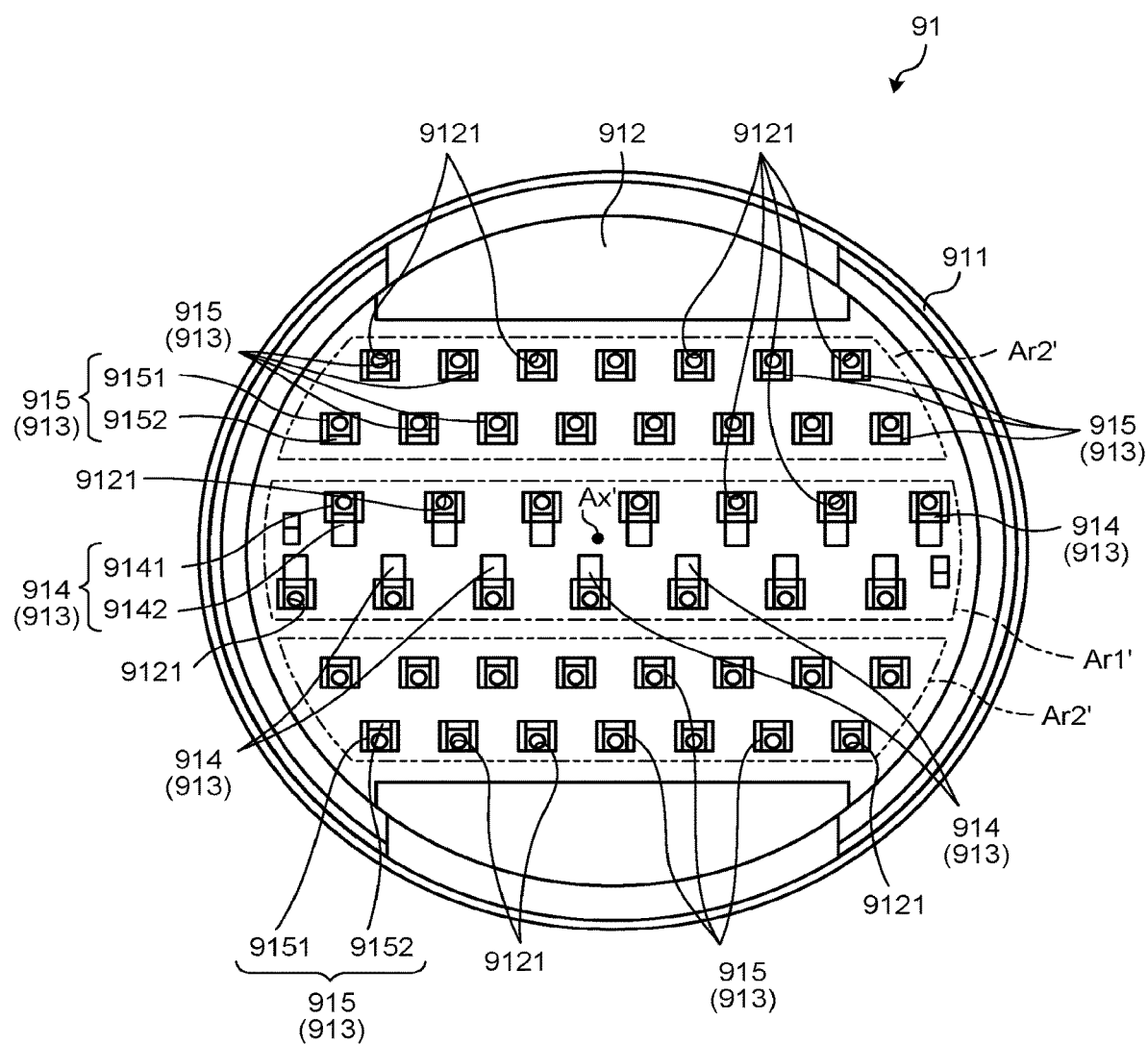
FIG. 9 illustrates an array of a plurality of contacts illustrated in FIG. 8.

FIG. 9 illustrates an array of the contacts 913.

In the following, first contacts 914 refer to the contacts 913 provided in a first region Ar1' illustrated with the dashed and single-dotted line in FIG. 9 among the contacts 913. Second contacts 915 refer to the contacts 913 provided in two second regions Ar2' illustrated with the dashed and double-dotted line in FIG. 9 among the contacts 913.

The first region Ar1' is opposite to the first region Ar1 illustrated in FIG. 4. The first region Ar1' is a strip-shaped region including the central axis Ax' in the second outer frame 911 when viewed in the direction of the central axis Ax' (FIG. 9) of the second outer frame 911 and extending in the horizontal direction in FIG. 9. The two second regions Ar2' are opposite to the respective two second regions Ar2 illustrated in FIG. 4. The two second regions Ar2' are regions other than the first region Ar1' in the second outer frame 911, which are parallel to the first region Ar1', and are strip-shaped regions extending in the horizontal direction in FIG. 9.

The first contacts 914 are arrayed in a similar manner to the first conductive pins 5224. In other words, the first contacts 914 are arranged side by side in two lines extending in the vertical direction of FIG. 9 in the first region Ar1'.

The second contacts 915 are arranged in a similar manner to the second conductive pins 5225. In other words, the second contacts 915 are arranged side by side in two lines extending in the vertical direction of FIG. 9 in each second regions Ar2'.

The first contacts 914 arrayed as described above have identical shapes. The following describes the shape of one of the first contacts 914.

As illustrated in FIG. 8 or 9, the first contacts 914 each include a first contact body 9141 and a first pin-shaped part 9142.

The first contact body 9141 is provided in the insertion holes 9121, has a substantially U shape when viewed in the direction of the central axis Ax', and extends along the central axis Ax'. The first contact body 9141 is electrically coupled with the conductive pins 5223 with its U-shaped inner periphery part being in contact with an outer periphery part of the conductive pins 5223 when the conductive pins 5223 are inserted into the insertion holes 9121.

The first pin-shaped part 9142 has a curved surface and protrudes from a U-shaped base end part of the first contact body 9141 toward the base end side (side on which the first and the second printed-circuit boards 92 and 93 are arranged) of the receptacle 91, and is formed as a plate spring that may be elasticity deformed.

The first contacts 914 arranged side by side in the first column on an upper side in FIG. 9 in the first region Ar1' are provided to the insertion holes 9121 so that the opening part of the U shape of each first contact body 9141 faces upward (the first pin-shaped part 9142 is positioned on a lower side). The first contacts 914 arranged side by side in the second column on the lower side are provided to the insertion holes 9121 so that the opening part of the U shape of each first contact body 9141 faces downward (the first pin-shaped part 9142 is positioned on the upper side).

The second contacts 915 arrayed as described above have identical shapes. The following describes the shape of one of the second contacts 915.

As illustrated in FIG. 8 or 9, the second contacts 915 each include a second contact body 9151 and a second pin-shaped part 9152.

The second contact body 9151 has the same shape and function as those of the first contact body 9141.

The second pin-shaped part 9152 linearly protrudes along the central axis Ax' from a base end part of the U shape of the second contact body 9151 toward the base end side of the receptacle 91.

The second contacts 915 arranged in the second region Ar2' on the upper side in FIG. 9 are provided to the insertion holes 9121 so that the opening part of the U shape of the second contact body 9151 faces upward (the second pin-shaped part 9152 is positioned on the lower side). The second contacts 915 arranged in the second region Ar2' on the lower side are provided to the insertion holes 9121 so that the opening part of the U shape of the second contact body 9151 faces downward (the second pin-shaped part 9152 is positioned on the upper side).

Configuration of First Printed-Circuit Board

Figure 10:
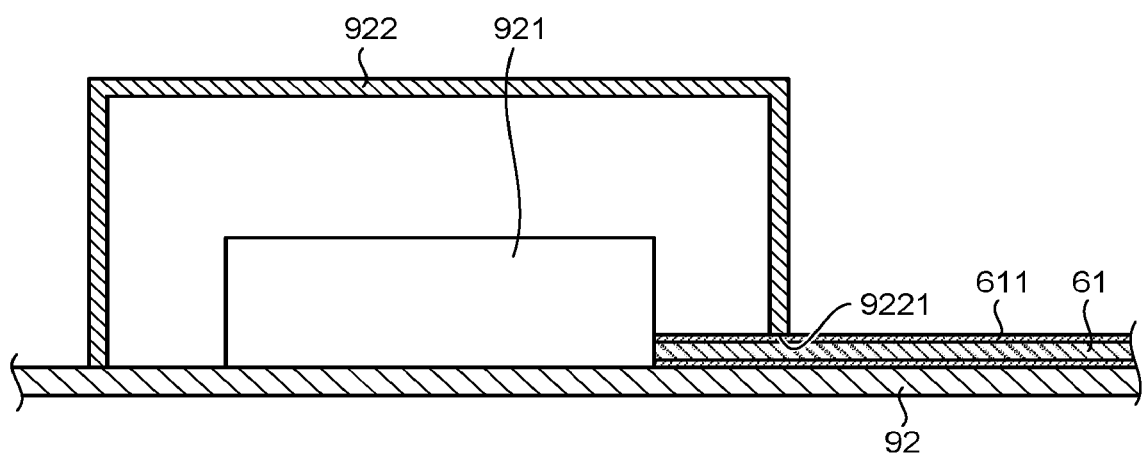
FIG. 10 is a sectional view schematically illustrating an electro-optic conversion element mounted on a first printed-circuit board illustrated in FIGS. 6 and 7.

FIG. 10 is a sectional view schematically illustrating an electro-optic conversion element 921 mounted on the first printed-circuit board 92.

The first printed-circuit board 92 has the functionality of a printed-circuit board according to the present disclosure, and is a rigid substrate on which, for example, the electro-optic conversion element 921 (FIG. 10) that converts an electric signal into an optical signal is mounted. The first printed-circuit board 92 is electrically coupled with the first contacts 914 of the receptacle 91, and relays, to the electro-optic conversion element 921, an image signal (electric signal) output from the image sensor 523 through the sealed-unit side printed-circuit board 524, the first conductive pins 5224, and the first contacts 914.

As illustrated in FIG. 10, the electro-optic conversion element 921 is coupled with the optical fibers (only one of the optical fibers 61 is illustrated in FIG. 10) each coated by the protection member 611 made of, for example, silicone resin. In other words, the electro-optic conversion element 921 converts an image signal (electric signal) into an optical signal and outputs the optical signal to the optical fibers 61.

In the present embodiment, only one electro-optic conversion element 921 is provided, but the present disclosure is not limited thereto, and a plurality of electro-optic conversion elements 921 may be provided. In the present embodiment, a plurality of optical fibers 61 are provided, but the present disclosure is not limited thereto, and a necessary number of optical fiber 61, for example, one optical fiber 61 may be provided.

As illustrated in FIG. 10, a shield case 922 is attached to a surface of the first printed-circuit board 92, on which the electro-optic conversion element 921 is mounted.

The shield case 922 is made of a metal material and has the functionality of a shield member that shields electromagnetic noise. As illustrated in FIG. 10, the shield case 922 has a substantially rectangular parallelepiped container shape without one side surface, and is attached to the surface of the first printed-circuit board 92 so that the electro-optic conversion element 921 is positioned in its inside (the shield case 922 covers an outer surface of the electro-optic conversion element 921). In other words, the shield case 922 shields influence of electromagnetic noise on the electro-optic conversion element 921 from the outside and the second printed-circuit board 93 and/or on other components from the electro-optic conversion element 921.

As illustrated in FIG. 10, a cut part 9221 into which the optical fibers 61 are inserted is formed on the shield case 922. In other words, the optical fibers 61 are coupled with the electro-optic conversion element 921 arranged inside the shield case 922 through the cut part 9221.

Another element (not illustrated) different from the electro-optic conversion element 921 is mounted at a position facing the electro-optic conversion element 921 on the back surface (surface opposite to the surface on which the electro-optic conversion element 921 is mounted) of the first printed-circuit board 92. A shield case 923 (FIGS. 6 and 7) having the same shape and function as those of the shield case 922 is attached to cover the outer surface of this another element.

As illustrated in FIG. 7, the first printed-circuit board 92 described above is arranged on the base end side of the receptacle 91 along the central axis Ax'.

Figure 11A:
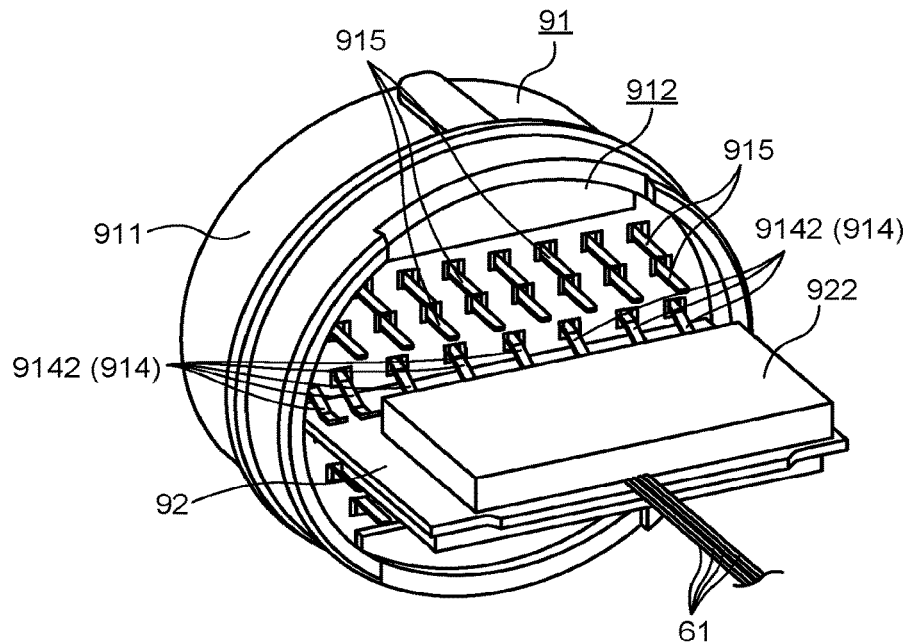
FIG. 11A is a perspective diagram illustrating that the first printed-circuit board is attached to the receptacle illustrated in FIGS. 6 and 7 when viewed from a base end side of the receptacle.
Figure 11B:
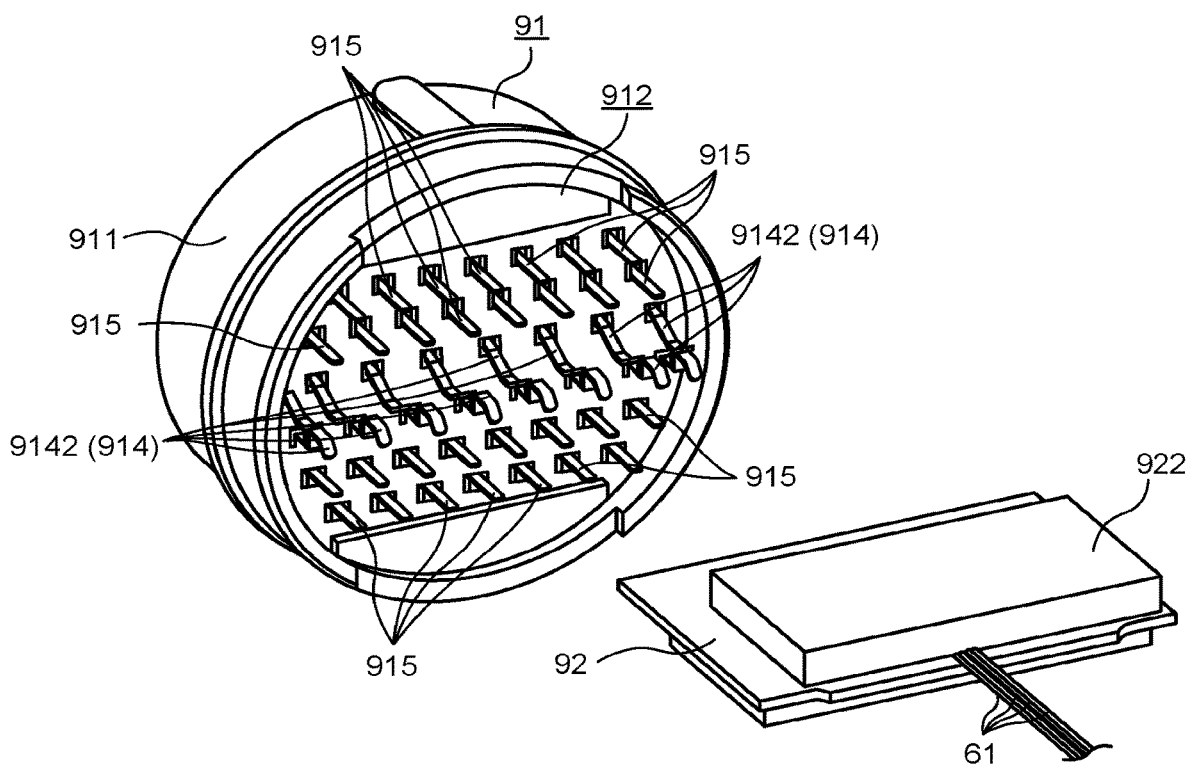
FIG. 11B is an exploded perspective view illustrating that the first printed-circuit board is removed from the receptacle illustrated in FIGS. 6 and 7 when viewed from the base end side of the receptacle.

FIG. 11A is a perspective diagram illustrating that the first printed-circuit board 92 is attached to the receptacle 91 when viewed from the base end side of the receptacle 91. FIG. 11B is an exploded perspective view illustrating that the first printed-circuit board 92 is removed from the configuration of FIG. 11A.

Specifically, the first printed-circuit board 92 is attached to the receptacle 91 as described below.

In other words, the first printed-circuit board 92 is inserted between the first contacts 914 (first pin-shaped parts 9142) in the first column on an upper side and the first contacts 914 (first pin-shaped parts 9142) in the second column on a lower side in FIGS. 11A and 11B. In this state, the first pin-shaped parts 9142 in the first and the second columns are pressed against the first printed-circuit board 92 and elastically deformed to hold the first printed-circuit board 92 therebetween. The first pin-shaped parts 9142 in the first and the second columns are electrically coupled with lands (not illustrated) formed on the front and back surfaces of the first printed-circuit board 92. Then, the first printed-circuit board 92 is fixed to the receptacle 91 by soldering the first pin-shaped parts 9142 and the lands in the above-described state.

Configuration of Second Printed-Circuit Boards

The two second printed-circuit boards 93 are each a flexible substrate at least part of which is bendable. The two second printed-circuit boards 93 relay, to the second contacts 915, a control signal or other signals (electric signals) output from the control device 8 through the electric signal cables 62. In other words, the control signal or other signals (electric signals) relayed to the second contacts 915 are output to the image sensor 523 through the second conductive pins 5225 and the sealed-unit side printed-circuit board 524.

These two second printed-circuit boards 93 have identical configurations. The following describes the configuration of one of the second printed-circuit board 93.

As illustrated in FIG. 6 or 7, the second printed-circuit board 93 includes a first coupling part 931 (FIG. 6), a second coupling part 932, and a bridge part 933 (FIG. 6) bridged between the first and the second coupling parts 931 and 932.

The first coupling part 931 has a shape corresponding to one of the second regions Ar2'. The first coupling part 931 has a plurality of holes 9311 (FIG. 6) corresponding to the respective second contacts 915 (second pin-shaped parts 9152) arranged in this second regions Ar2'.

As illustrated in FIG. 6, the first coupling part 931 is placed on an end face of the insulator 912 on a base end side while the second contacts 915 are inserted into the respective holes 9311, and fixed to the receptacle 91 by soldering lands 9312 provided around the holes 9311 and the second pin-shaped parts 9152.

As illustrated in FIG. 6 or 7, the second coupling part 932 is arranged at a position overlapping the first printed-circuit board 92 in FIG. 6 or 7 by folding the bridge part 933 for the first coupling part 931 fixed to the receptacle 91.

As illustrated in FIG. 6, a plurality of lands 9321 each having a substantial rectangular shape are formed on a surface of the second coupling part 932. The second coupling part 932 is electrically coupled with the electric signal cables 62 by soldering the electric signal cables 62 with the lands 9321.

Configuration of Module-Side Case

As illustrated in FIG. 7, the module-side case 94 has a tubular shape, and has an opening part (opening part on the left side in FIG. 7) on one end engaged with the base end side of the receptacle 91 (side opposite to the side with which the sealing connector 522 are coupled). The module-side case 94 covers the first and the second printed-circuit boards 92 and 93, and a part of the composite cable 6 (parts of the optical fibers 61 and the electric signal cables 62).

The module-side case 94 has a plurality of fill holes 941 formed on the other end (on the right side in FIG. 7). The fill holes 941 communicate between the inside and outside of the module-side case 94 as illustrated in FIG. 7. The filling member 95 is inserted into the fill holes 941.

Configuration of Filling Member

As illustrated in FIG. 7, the filling member 95 is filled inside the module-side case 94. In the present embodiment, the filling member 95 is a thermal curing resin such as epoxy resin and fluorine resin each having a low moisture permeability and a high barrier against gas.

The material of the filling member 95 is not limited to epoxy resin or fluorine resin, but is, for example, silicone resin.

Figure 12:
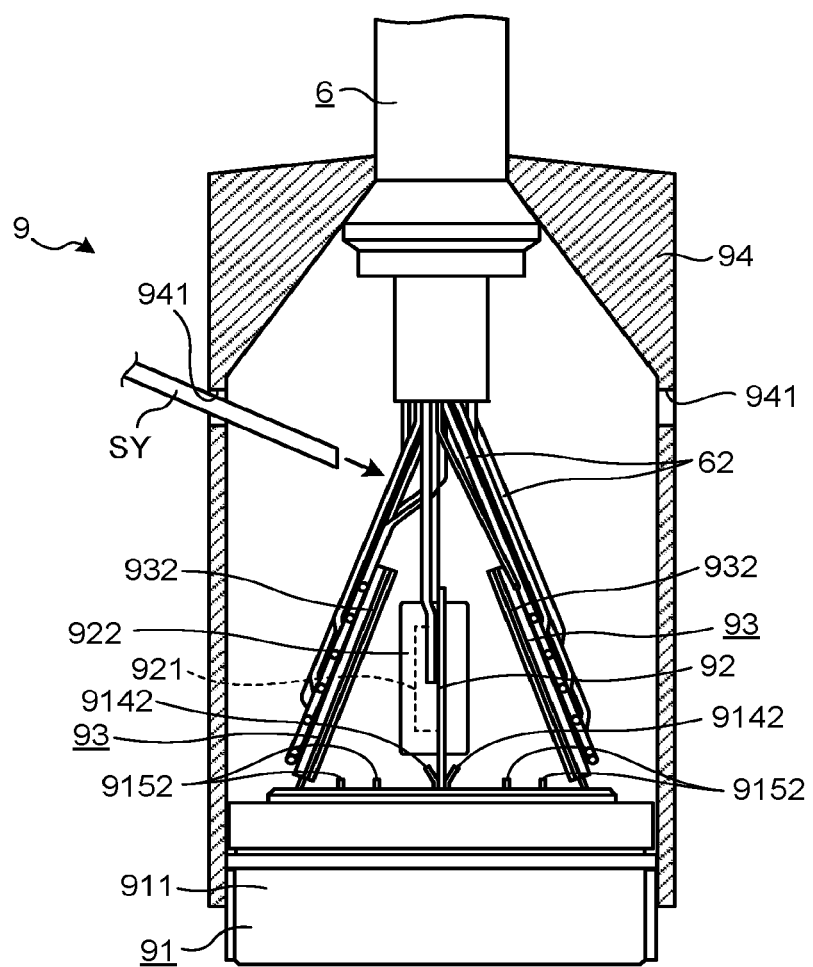
FIG. 12 illustrates a method of filling inside a second case illustrated in FIGS. 5 and 7 with a filling member.

FIG. 12 illustrates a method of filling inside the module-side case 94 with the filling member 95. Specifically, FIG. 12 corresponds to FIG. 7.

A worker inserts the composite cable 6 into the module-side case 94, and attaches the first and the second printed-circuit boards 92 and 93, which are attached to the composite cable 6, to the receptacle 91 by soldering as described above. Then, the worker engages the base end side of the receptacle 91 with an opening part of the module-side case 94 on one end (opening part on a lower side in FIG. 12).

Next, as illustrated in FIG. 12, the worker places the receptacle 91 on a desk or the like in such a manner that the receptacle 91 is on a lower side of the module-side case 94. Then, the worker inserts the needle of an injector SY (FIG. 12) filled with uncured thermal curing resin (the filling member 95) in advance into one of the fill holes 941 of the module-side case 94, and fills inside the module-side case 94 with this thermal curing resin. When filled at an angle illustrated in FIG. 12, the uncured thermal curing resin (filling member 95) is gradually accumulated from one end side of the module-side case 94 (lower side in FIG. 12), and fills up to the other end of the module-side case 94 (FIG. 7).

Next after the filling with the uncured thermal curing resin (filling member 95), the worker cures this thermal curing resin by heating.

Filling inside the module-side case 94 in this manner, the filling member 95 seals the electro-optic conversion element 921 while covering the outer surface of the shield case 922 on the first printed-circuit board 92 (FIG. 7). In other words, the module-side case 94, the shield case 922, the first printed-circuit board 92, and the filling member 95 form a sealed space (the inside of the shield case 922) so that the electro-optic conversion element 921 is arranged (sealed) in this space, and thus have the functionality of a sealing member according to the present disclosure. The module-side case 94 and/or the shield case 922 have the functionality of a second case according to the present disclosure.

The above-described space (inside of the shield case 922) is held watertightly by the filling member 95.

The filling member 95 entirely fills inside the module-side case 94, but the present disclosure is not limited thereto. The filling member 95 may fill at least the openings of the module-side case 94 and the shield case 922.

The above-described space (inside of the shield case 922) is held watertightly by the filling member 95, but a space in which the electro-optic conversion element 921 is provided may be held airtightly by configuring, for example, the module-side case 94 to be airtight. In this case, the inside of the module-side case 94 does not need to be filled with the filling member 95.

In the camera head 5 according to the present embodiment described above, the image sensor 523 is arranged inside the sealed-unit side case 521 which is sealed by the sealing connector 522. The electro-optic conversion element 921 (the first printed-circuit board 92) is arranged outside the sealed-unit side case 521. In other words, an image signal from the image sensor 523 is transmitted, as an electric signal, to the outside of the sealed-unit side case 521 through the conductive pins 5223 (first conductive pins 5224) of the sealing connector 522, and converted into an optical signal at the electro-optic conversion element 921. The electro-optic conversion element 921 is arranged in the space (inside of the shield case 922) sealed by the module-side case 94, the shield case 922, the first printed-circuit board 92, and the filling member 95. In other words, the electro-optic conversion element 921 is sealed in such a manner that its outer surface is covered by the filling member 95 on the first printed-circuit board 92.

Thus, the camera head 5 according to the present embodiment achieves a small configuration that optically transmits an image signal at low cost. In addition, the module-side case 94, the shield case 922, the first printed-circuit board 92, and the filling member 95 may protect the electro-optic conversion element 921 against a medicinal solution used in sterilization involving wiping and liquid immersion and high-temperature and high-pressure vapor in autoclave processing.

In the camera head 5 according to the present embodiment, the filling member 95 fills inside the module-side case 94.

Thus, the filling member 95 may protect the entire members (the first and the second printed-circuit boards 92 and 93, and part of the composite cable 6 (part of the optical fibers 61 and the electric signal cables 62)) arranged inside the module-side case 94 against high-temperature and high-pressure vapor in autoclave processing.

In the camera head 5 according to the present embodiment, the shield case 922 covering the outer surface of the electro-optic conversion element 921 is attached to the first printed-circuit board 92. While covering the outer surface of the shield case 922, the filling member 95 seals the electro-optic conversion element 921.

Thus, when the inside of the module-side case 94 is filled with the uncured thermal curing resin (filling member 95) and cured, stress due to cure shrinkage of this thermal curing resin is not directly applied to the electro-optic conversion element 921. Accordingly, no unwanted stress is applied to coupling parts between the electro-optic conversion element 921 and the first printed-circuit board 92 and between the electro-optic conversion element 921 and each optical fiber 61, thereby sufficiently maintaining the quality of the camera head 5 after assembly.

When the coupling parts between the electro-optic conversion element 921 and the first printed-circuit board 92 and between the electro-optic conversion element 921 and each optical fiber 61 are reinforced by reinforcing members or the like, and the strength of each coupling part is sufficiently maintained, the filling member 95 may fill inside the shield case 922. Moreover, when the shield case 922 is unnecessary because the strength of this coupling part is sufficiently maintained, and influence of electromagnetic noise on the electro-optic conversion element 921 and/or due to the electro-optic conversion element 921 is sufficiently small, the outer surface of the electro-optic conversion element 921 on the first printed-circuit board 92 coupled with the optical fibers 61 may be directly covered and sealed by the filling member 95.

In the camera head 5 according to the present embodiment, each optical fiber 61 is coated by the protection member 611 before the uncured thermal curing resin (filling member 95) fills inside the module-side case 94.

Thus, when the inside of the module-side case 94 is filled with the uncured thermal curing resin (filling member 95) and cured, stress due to cure shrinkage of this thermal curing resin is not directly applied to the optical fibers 61. Accordingly, no unwanted stress is applied to the coupling part between each optical fiber 61 and the electro-optic conversion element 921, and no optical fiber 61 is buckled, thereby sufficiently maintaining the quality of the camera head 5 after assembly.

In the camera head 5 according to the present embodiment, the sealing connector 522 that transmits only an electric signal is adopted as the blocking part according to the present disclosure.

However, a sealing connector with an additional configuration for transmitting an optical signal would have a complicated configuration, resulting in an increase in the cost and size of the sealing connector. In contrast, using the sealing connector 522 that transmits only an electric signal may reduce an increase in the cost and size of the sealing connector 522, thereby reducing an increase in the cost and size of the camera head 5.

In the camera head 5 according to the present embodiment, the total number of effective pixels of the image sensor 523 is eight megapixels or larger. When the data amount of image signals from the image sensor 523 is large as in this example, optical transmission of the image signals is particularly advantageous.

In the endoscope device 1 according to the present embodiment, the display device 7 has a monitor size of 55 inches or larger. When the monitor size is 55 inches or larger as in this example, an operator has an extremely high sense of immersion into a displayed image, and thus optical transmission of a large data amount of image signals is particularly advantageous to display a high-definition image on the display device 7 having such a monitor size.

Other Embodiments

While the present disclosure has been described with reference to exemplary embodiments, it is to be understood that the disclosure is not limited to the disclosed exemplary embodiment.

Figure 13:
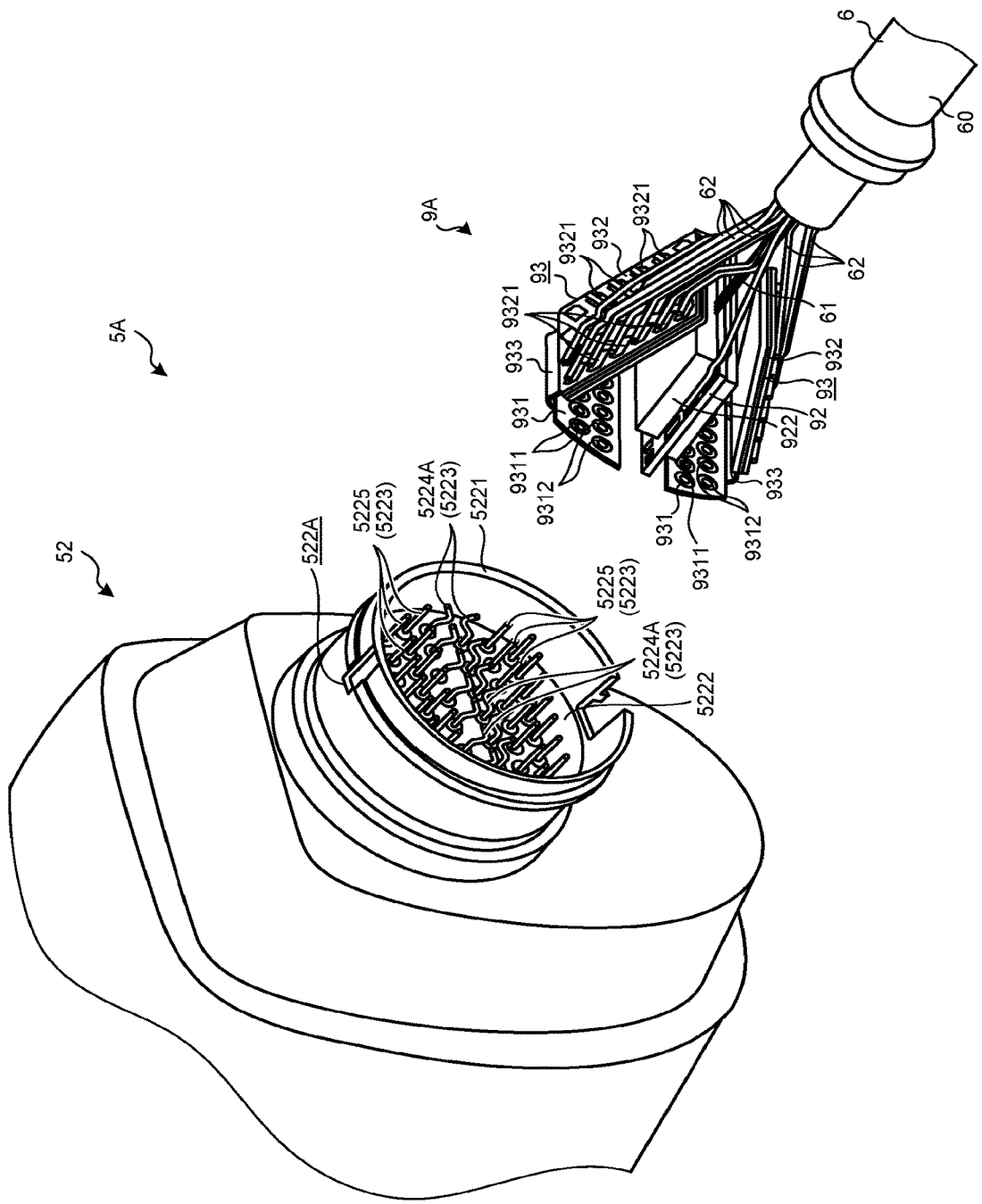
FIG. 13 illustrates modification 1 of the embodiment of the present disclosure.
Figure 14:
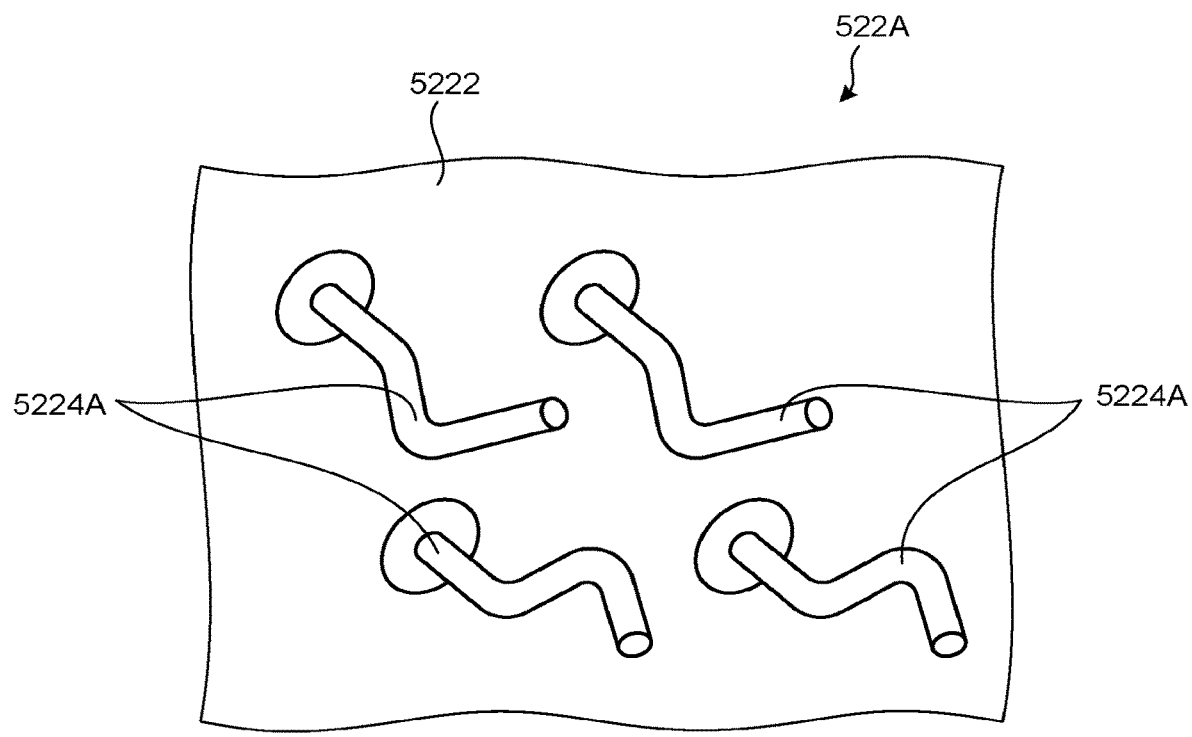
FIG. 14 illustrates the shapes of first conductive pins illustrated in FIG. 13.

FIG. 13 illustrates modification 1 of the embodiment according to the present disclosure. Specifically, FIG. 13 is an exploded perspective view of a camera head 5A according to the present modification 1 when viewed from a base end side. FIG. 14 illustrates the shapes of first conductive pins 5224A illustrated in FIG. 13.

For the purpose of illustration, FIG. 13 does not illustrate the module-side case 94 and the filling member 95.

In the embodiment described above, the electro-optic combined module 9 includes the receptacle 91 and is detachably coupled with the sealed unit 52 (sealing connector 522) through this receptacle 91, but the present disclosure is not limited thereto.

For example, as illustrated in FIG. 13, an electro-optic combined module 9A that does not include the receptacle 91 included in the electro-optic combined module 9 described in the above embodiment may be used, and the first and the second printed-circuit boards 92 and 93 of this electro-optic combined module 9A may be directly attached to a sealing connector 522A by soldering.

In the sealing connector 522A according to the present modification 1, the first conductive pins 5224 have shapes different from those of the sealing connector 522 described in the above embodiment.

Specifically, similarly to the first pin-shaped part 9142, as illustrated in FIG. 14, the first conductive pins 5224A according to the present modification 1 on an external side (side with which the electro-optic combined module 9A is coupled) of the sealed unit 52 each have a curved surface and protrude toward the outside of the sealed unit 52, and are each formed as a plate spring that may be elastically deformed.

In other words, the first printed-circuit board 92 is inserted between the first conductive pins 5224A in the first column on an upper side in FIG. 14 and the first conductive pins 5224A in the second column on a lower side. In this state, the first conductive pins 5224A in the first and the second columns are pressed against the first printed-circuit board 92 and elasticity deformed to hold the first printed-circuit board 92 therebetween. The first conductive pins 5224A in the first and the second columns are electrically coupled with lands (not illustrated) formed on the front and back surfaces of the first printed-circuit board 92. Then, the first printed-circuit board 92 is directly fixed to the sealing connector 522A by soldering the first conductive pins 5224A and the lands in the above-described state.

The two second printed-circuit boards 93 are directly fixed to the sealing connector 522A by soldering the lands 9312 provided around the holes 9311 of the first coupling part 931 and the second conductive pins 5225 while the second conductive pins 5225 are inserted into the holes 9311 and this first coupling part 931 is placed on an external end face of the sealed unit 52 of the plate 5222.

Although not specifically illustrated, the module-side case 94, which covers the first and the second printed-circuit boards 92 and 93 and the part of the composite cable 6 (part of the optical fibers 61 and the electric signal cables 62), has its opening part on one end engaged with the sealing connector 522A. Similarly to the embodiment described above, the filling member 95 fills a space surrounded by the sealing connector 522A and the module-side case 94 (space in which the first and the second printed-circuit boards 92 and 93 and part of the composite cable 6 are arranged).

FIG. 15 illustrates modification 2 of the embodiment according to the present disclosure. Specifically, FIG. 15 schematically illustrates an endoscope device 1B according to the present modification 2.

In the embodiment described above, the present disclosure is applied to the endoscope device 1 in which the insertion unit 2 and the camera head 5 are detachably coupled, but is not limited thereto.

For example, the present disclosure is applicable to the endoscope device 1B including an endoscope image-capturing device 5B illustrated in FIG. 15.

Specifically, as illustrated in FIG. 15, the endoscope device 1B includes the endoscope image-capturing device 5B in addition to the composite cable 6, the display device 7, and the control device 8 described in the above embodiment.

As illustrated in FIG. 15, the endoscope image-capturing device 5B includes a sealed unit 52B in addition to the electro-optic combined module 9 described in the above embodiment.

As illustrated in FIG. 15, the sealed unit 52B includes a sealed-unit side case 525, an optical system 526, and a printed-circuit board 527 in addition to the sealing connector 522, the image sensor 523, and the sealed-unit side printed-circuit board 524 described in the above embodiment.

The sealed-unit side case 525 has the functionality of the first case according to the present disclosure. The sealed-unit side case 525 is made of a metal material and has a substantially tubular shape.

The sealed-unit side case 525 has an elongate shape at a part on one end (part on the left side in FIG. 15), and serves as an insertion unit 5251 inserted into the inside of the living body. At a part on the other end (part on the right side in FIG. 15), the sealed-unit side case 525 has a diameter larger than that of the insertion unit 5251, and serves as a hold part 5252 held by a doctor, for example.

As illustrated in FIG. 15, the insertion unit 5251 of the sealed-unit side case 525 has an opening 5251B sealed by a translucent member 5253 such as glass. The hold part 5252 has an opening 5252B engaged with and sealed by the sealing connector 522. The inside of the sealed-unit side case 525 is held airtightly and watertightly by the translucent member 5253 and the sealing connector 522.

As illustrated in FIG. 15, the insertion unit 5251 houses the optical system 526 and the image sensor 523.

The optical system 526 is arranged adjacent to the translucent member 5253 on a head side of the insertion unit 5251. The optical system 526 condenses an object image through the translucent member 5253 to image this object image on the imaging plane of the image sensor 523.

The image sensor 523 is the same as the image sensor 523 described in the above embodiment, and is arranged adjacent to the optical system 526 on the head side of the insertion unit 5251.

As illustrated in FIG. 15, the hold part 5252 houses the printed-circuit board 527 and the sealed-unit side printed-circuit board 524.

The printed-circuit board 527 is electrically coupled with the image sensor 523 through a signal line SL (FIG. 15) distributed inside the sealed-unit side case 525, and is electrically coupled with the sealed-unit side printed-circuit board 524 attached to the sealing connector 522. The printed-circuit board 527 provides predetermined processing (A/D conversion, for example) on an image signal output from the image sensor 523 and outputs the image signal to the sealed-unit side printed-circuit board 524 (first conductive pins 5224). The printed-circuit board 527 drives the image sensor 523 through the signal line SL in response to a control signal output from the control device 8 through the composite cable 6, the electro-optic combined module 9, the second conductive pins 5225, and the sealed-unit side printed-circuit board 524.

In the embodiment described above and its modifications 1 and 2, the filling member 95 substantially thoroughly fills inside the module-side case 94, but the present disclosure is not limited thereto. When the electro-optic conversion element 921 on the first printed-circuit board 92 has its outer surface covered and sealed by resin, the electro-optic conversion element 921 may be sealed by potting, for example.

In the embodiment described above and its modifications 1 and 2, the camera heads 5 and 5A and the endoscope image-capturing device 5B perform signal communication between the insides (the image sensor 523) of the sealed units 52 and 52B and the electro-optic combined module 9 (the first and the second printed-circuit boards 92 and 93) through the conductive pins 5223 of the sealing connectors 522 and 522A and the contacts 913 of the receptacle 91, but the present disclosure is not limited thereto. The signal communication may be performed by wireless signal communication using, for example, a magnetic field. This eliminates the need to provide the conductive pins 5223 and the contacts 913 in the sealed units 52 and 52B and the electro-optic combined module 9.

The electro-optic conversion element 921 includes, for example, a light emitting unit such as a laser diode and emits communication light such as laser light from this light emitting unit. Performance degradation of optical transmission of this light emitting unit may be caused by a reduction in the amount of emission light due to long-time drive. Thus, the endoscope devices 1 and 1B in the embodiment described above and its modifications 1 and 2 may be provided with a replacement notifying unit that notifies replacement timing of the light emitting unit to an operator or a serviceperson.

Specifically, the replacement notifying unit includes an energization time counting unit that counts an energization time of the light emitting unit, a non-transitory memory that stores energization time information on the energization time obtained by this energization time counting unit, a comparing unit that compares an energization time based on the energization time information stored in this non-transitory memory to a predetermined replacement time, and a notifying unit that notifies, when this comparing unit determines that the energization time exceeds the predetermined replacement time, the operator or the serviceperson of this determination.

Timing of the notification by the notifying unit may be timing when the energization time exceeds the predetermined replacement time, timing before the energization time exceeds the predetermined replacement time (the energization time is reaching the predetermined replacement time), or both. The predetermined replacement time described above may be set as appropriate for the timing.

The energization time counting unit may be replaced with a light quantity measuring unit that measures the light quantity of at least part of light from the light emitting unit, and may perform a notification when this light quantity is equal to or smaller than a predetermined replacement light quantity.

In response to the notification by the replacement the notifying unit, the operator or the serviceperson replaces the electro-optic conversion element 921. A part to be replaced may be the entire composite cable 6 including the electro-optic conversion element 921, only the electro-optic conversion element 921, or the entire electro-optic combined modules 9 and 9A. When the electro-optic conversion element 921 is provided to the camera head 5, the camera head 5 may be replaced. This enables optical transmission constantly without performance degradation.

In an endoscope image-capturing device according to the present disclosure, an image sensor is arranged in a first case the inside of which is sealed. An electro-optic conversion element is arranged outside the first case, receives an image signal from the image sensor arranged inside the first case through wireless communication or through a sealing connector such as a hermetic connector attached to the first case, and converts this image signal into an optical signal. The electro-optic conversion element is sealed by a sealing member.

Thus, the endoscope image-capturing device according to the present disclosure may achieve a small configuration that optically transmits an image signal at low cost and may protect, with the sealing member, the electro-optic conversion element against a medicinal solution used in sterilization involving wiping and liquid immersion and high-temperature and high-pressure vapor in autoclave processing.

An endoscope device according to the present disclosure includes the endoscope image-capturing device described above and thus provides the same advantageous effect as the above-described advantageous effect of the endoscope image-capturing device.

It should be understood by those skilled in the art that various modifications, combinations, sub-combinations and alterations may occur depending on design requirements and other factors insofar as they are within the scope of the appended claims or the equivalents thereof.

What is claimed is:

1. An endoscope image-capturing device comprising:
   a first case having an outer surface to be held by a user when the user operates the endoscope image-capturing device, an inside of the first case being sealed;
   an image sensor arranged inside the first case;
   a second case that partially overlaps with the first case;
   an electro-optic conversion element arranged inside the second case and configured to convert an electric image signal output from the image sensor into an optical signal, the image sensor inside the first case and the electro-optic conversion element inside the second case being electrically connected with each other when in operation; and
   a sealing member sealing the electro-optic conversion element arranged inside the second case, wherein
   the image sensor is not arranged inside the second case, and
   the second case is not arranged entirely inside the first case.

2. The endoscope image-capturing device according to claim 1, wherein the sealing member includes resin that covers the electro-optic conversion element and seals the electro-optic conversion element.

3. The endoscope image-capturing device according to claim 2, wherein
   the resin fills at least an opening of the second case.

4. The endoscope image-capturing device according to claim 1, further comprising:
   a blocking part blocking an opening of the first case to seal the inside of the first case; and
   a printed-circuit board that is arranged outside the first case and on which the electro-optic conversion element is mounted, wherein
   the blocking part is provided with a terminal configured to electrically couple the image sensor arranged inside the first case and the printed-circuit board arranged outside the first case.

5. The endoscope image-capturing device according to claim 4, wherein the blocking part is a sealing connector.

6. The endoscope image-capturing device according to claim 1, wherein the inside of the first case is held airtightly.

7. An endoscope device comprising the endoscope image-capturing device according to claim 1.

8. The endoscope device according to claim 7, wherein the image sensor has number of effective pixels of eight megapixels or larger.

9. The endoscope device according to claim 8, further comprising a display configured to display an image captured by the endoscope image-capturing device, wherein the display has a monitor size of 55 inches or larger.

10. The endoscope image-capturing device according to claim 1, wherein the sealing member entirely seals the electro-optic conversion element.

11. The endoscope image-capturing device according to claim 1, wherein the sealing member seals the electro-optic conversion element to enable autoclave processing.

12. The endoscope image-capturing device according to claim 1, wherein the sealing member fills a space inside the second case.

13. The endoscope image-capturing device according to claim 1, wherein the first case and the second case are connected via a connector.

14. The endoscope image-capturing device according to claim 1, further comprising a switch exposed on the outer surface of the first case, the switch being to be operated by the user.

15. The endoscope image-capturing device according to claim 1, wherein the second case is detachable from the first case.

* * * * *